United States Patent [19]

Hodam, Jr. et al.

[11] Patent Number: 5,348,678
[45] Date of Patent: Sep. 20, 1994

[54] POLYMER-BASED CLEANING AND LUBRICATING COMPOSITION

[75] Inventors: Robert H. Hodam, Jr., Austin, Tex.; Marvin H. Gold, Sacramento, Calif.

[73] Assignee: Medical Polymers Technologies, Inc., Austin, Tex.

[21] Appl. No.: 977,608

[22] Filed: Nov. 17, 1992

Related U.S. Application Data

[63] Continuation-in-part of Ser. No. 793,596, Nov. 18, 1991.

[51] Int. Cl.$^5$ ............................................. C11D 3/48
[52] U.S. Cl. ..................... 252/106; 252/174.21; 252/174.23; 252/DIG. 2; 252/547; 252/174.15; 424/405; 514/694; 514/705; 514/693; 514/731; 514/724
[58] Field of Search .............. 252/106, 174.21, 174.23, 252/DIG. 2, 547, 174.15; 424/405; 514/694, 705, 693, 731, 724

[56] References Cited

U.S. PATENT DOCUMENTS

| | | | |
|---|---|---|---|
| 4,093,744 | 6/1978 | Winicov et al. | |
| 4,173,653 | 11/1979 | Law | 434/333 |
| 4,347,237 | 8/1982 | Evenstad et al. | 424/78 |
| 4,389,320 | 6/1983 | Clampitt | 252/8.55 R |
| 4,478,853 | 10/1984 | Chaussee | 424/358 |
| 4,548,812 | 10/1985 | Foley | 424/78 |
| 4,551,148 | 11/1985 | Riley, Jr. et al. | 604/890 |
| 4,629,623 | 12/1986 | Balazs et al. | 424/78 |
| 4,632,772 | 12/1986 | Garabedian et al. | 252/106 |
| 4,753,844 | 6/1988 | Jones et al. | 428/288 |
| 4,804,685 | 2/1989 | Jacobs et al. | 514/698 |
| 4,880,558 | 11/1989 | Jost et al. | 252/174.23 |
| 4,976,953 | 12/1990 | Orr et al. | 424/47 |
| 5,004,757 | 4/1991 | Boucher | |
| 5,093,396 | 3/1992 | Calhoun et al. | 524/204 |
| 5,100,657 | 3/1992 | Ansher-Jackson et al. | 424/70 |
| 5,190,679 | 3/1993 | McDonald | 252/41 |

*Primary Examiner*—Anthony McFarlane
*Assistant Examiner*—Nhat D. Phan
*Attorney, Agent, or Firm*—Winstead Sechrest & Minick

[57] ABSTRACT

Polymer-based composition effective for disinfecting and for sterilizing plus cleaning and/or lubricating devices. The composition contains, in solution, a hydrophilic polymer serving as a water-based lubricant, a disinfectant, and a surfactant. The addition of a hydrophilic polymer forms an anti-corrosive formula for sterilizing, disinfecting, cleaning, and lubricating devices including medical and dental devices where the efficacy of cleaning and sterilizing is enhanced by the addition of a hydrophilic polymer.

6 Claims, No Drawings

POLYMER-BASED CLEANING AND LUBRICATING COMPOSITION

REFERENCE TO RELATED APPLICATIONS

This is a continuation-in-part application of pending U.S. Ser. No. 07/793,596, now pending, entitled, "Disinfectant Mixture Containing Water Soluble Lubricating and Cleaning Agents and Method", filed Nov. 18, 1991.

FIELD OF THE INVENTION

This invention generally relates to a disinfectant mixture containing water-soluble lubricating and cleaning agents. More particularly the present invention relates to a composition for sterilizing, disinfecting, cleaning and lubricating medical and dental devices.

BACKGROUND OF THE INVENTION

Handpieces are the power units that a dentist utilizes in driving the burs used in the practice of the profession. Most high-speed devices in use today in dentistry are powered by compressed air driving a high speed turbine, which in turn is connected to the various tools and burs used in the patient's mouth. Such turbines may operate at speeds over 400,000 rpm. The bearings in these turbines are usually lubricated with petroleum oils, although there are on the market certain units having ceramic bearings, which are reputed to operate without any lubrication.

Nevertheless, when oil is used as a lubricant there are occasions when the oil may be atomized onto or be splashed onto a freshly cleaned or drilled tooth surface, thereby inhibiting good bonding with fillings or plastic coatings used in the reconstruction or preservation of the tooth. Therefore, it would be beneficial to avoid any condition which might allow oil to enter the mouth during dental procedures. Also, oil stains the device, forming a sticky varnish when heated in an autoclave during sterilization.

Currently, medical devices are typically cleaned daily or weekly by soaking in alcohol, acetone or disinfectant. Typically, there is no cleaning of the device between patients except wiping off the outside. In addition, there is no disinfection or sterilization of devices between patients and there is no lubrication of the devices between patients. In fact, it is impractical to lubricate dental handpieces between patients because typical lubricants used are oil based and have a tendency to cause bonding problems on the teeth due to oil which may come in contact with the enamel on the teeth.

There currently is no practical method to disinfect or sterilize medical devices between patients because chemical baths, chemclaves or autoclaves damage the dental handpieces. In addition, the chemclaves and autoclaves do not remove foreign material such as protein, organisms, and blood from within the dental handpiece. There is therefore a need for a cleaner, which may be a disinfectant and/or sterilant, and lubricant to overcome these difficulties and to make it possible for such devices to be disinfected, lubricated and cleaned between patients.

SUMMARY OF THE INVENTION

Generally, the disinfectant mixture of the present invention contains water-soluble lubricating and cleaning agents and is comprised of a hydrophilic polymer. The addition of hydrophilic polymers enhances the performance of both surfactants and sterilants. Exemplary polymers include polyethylene oxides, polyacrylamides, polyvinyl alcohols, polyacrylic acids, polyvinyl pyrrolidones, cellulose derivatives (e.g., methyl cellulose, hydroxethyl cellulose, carboxymethyl cellulose, and the like), polyethylene glycols, and water-soluble silicones or fluoro compounds, which can be used singly or in combination. The mixture also is comprised of a broad range of disinfectants/sterilants which contain anti-microbial chemicals and which are mixable with the hydrophilic polymer to form an aqueous solution for the purpose of disinfection/sterilization and cleaning/lubrication. Disinfectants commonly available which can be used with water-based lubricants include peracetic acids, phenols, alcohols, formaldehyde, glutaraldehyde, quaternary ammonium halides, chlorohexidine, and iodophors. One or more of these disinfectants can be utilized with a hydrophilic polymer or a combination of hydrophilic polymers to which, if desired, a surfactant can be added.

Specifically, the inventive composition comprises by weight 0.1 to 7.5 percent of a hydrophilic polymer which serves as a water-based lubricant, and 1 to 5 percent by weight of a disinfectant, with the balance being deionized water. Also, 0.1 to 2.5 percent by weight of a surfactant, an anti-oxidant in the range of 0.25 to 1 percent and a dispersant in the range of 1 to 10 percent by weight can be utilized.

DETAILED DESCRIPTION OF THE INVENTION

The present invention involves the addition of hydrophilic polymers with known sterilizing chemicals and surfactants to achieve a potentiation effect which improves anti-microbial efficacy of the sterilants, and cleaning efficacy of the surfactants for the purpose of sterilizing and cleaning out organic debris, such as blood, from medical and dental devices.

The addition of, e.g., polyethylene oxide, to disinfectants also provides a multifunctional product. That is, this invention combines lubricating, disinfecting, sterilizing and cleaning features into one product. The addition of a selected polymer serves to concentrate any water soluble sterilant directly onto microorganisms, thus enhancing the biocidal effect of the sterilant.

The polymer of the present invention may also function as a vehicle for concentrating a biocidal chemical on a microorganism. Polymers will adhere to the surface of bacteria, viruses, parasites, plant-like cells, and spores through forces of association and interpenetration of proteins on the cell surface. The selected surfactants enhance this association by allowing close proximity of the polymer to the surface of the organism.

Depending on the microorganism morphology and cell wall biochemistry, the hydrophilic polymers of the present invention have greater or lesser affinity for association. Therefore it is important to include at least one lipophilic surfactant and at least one hydrophilic surfactant to ensure proper wetting of the surface of the organism to maximize the interpenetration and association of the selected polymer. Typically, one might use a combination of sodium laurylsulfate and a polyethoxylated nonylphenol, or sodium dioctyl sulfosuccinate and ammonium polyethoxylated dodecyl phosphate, or octadecyl benzyl dimethyl ammonium chloride and polyethoxylated sorbitan laureate. Once the selected polymer reaches the surface of the organism, a film of polymer forms around the organism. This has two useful functions: to improve cleaning out of organic debris (blood, viable and non-viable organisms, etc.); and, to increase the efficacy of the biocidal active ingredient.

Cleaning is enhanced by incorporating hydrophilic polymers, such as polyethylene oxide or polyacrylamide, because the debris, being covered by a fully hydrated polymer in solution, cannot easily attach to another such piece of debris or to a hard surface such as internal parts of a medical device. Also, cleaning is enhanced because the selected polymer forms a film on internal hard surfaces which prevents blood, organisms and inert debris from attaching or drying onto internal hard surfaces of a medical device.

Sterilization is enhanced by the addition of hydrophilic polymers, such as polyethylene oxide or polyacrylamide, because there are forces of association and hydrogen bonding between water soluble sterilants and the polymers so that chemical biocides tend to concentrate around the polymer. When a selected polymer, carrying the biocide, comes in contact with an organism it attaches as described above, thus concentrating the biocide onto the organism to be killed. For this reason the selection of a specific biocide is not critical to this invention. Any water soluble biocide used with any hydrophilic polymer would behave as described above with varying degrees of increased efficacy.

Generally, the composition of the present invention consists of a water-soluble or water-dispersible disinfecting and/or sterilizing agent, one or more surfactants and a water-soluble polymer having lubricating characteristics. Preferably, the hydrophilic polymer is selected from polyethylene oxides, polyacrylamides, polyvinyl alcohols, polyacrylic acids, polyvinyl pyrrolidones, cellulose derivatives (e.g. methyl cellulose, hydroxyethyl cellulose, carboxymethyl cellulose, and the like), polyethylene glycols, and water-soluble silicones or fluoro compounds.

Preferably, the sterilizing disinfecting agent is selected from the group of agents including alcohols, peracetic acid, glutaraldehyde, formaldehyde, phenols, chlorohexidine, polyvinyl pyrrolidone-iodine complexes or other iodophors. One or more of any of the above agents may be used in preparing the present invention composition. In a preferred form of the invention, glutaraldehyde is used at concentrations in the order of 1 to 5 percent by weight. More particularly, glutaraldehyde is used in concentrations of 2.5 to 4.5 percent by weight.

In a preferred form of the invention, polyethylene oxides are used in the molecular weight range of 8,000 to 5,000,000 and/or polyacrylamides in the molecular weight range of 200,000 to 15,000,000. Concentrations of polyethylene oxides in the range of 0.1 to 8.0 percent, depending upon molecular weight, are applicable. Similarly, when polyacrylamides are used, concentrations of about 0.05 to 8.0 percent, preferably about 0.2 to 8.0 percent, are applicable depending on molecular weight.

However, it may not be practical to use systems involving polyacrylamides with aldehydes due to the reactivity of the aldehyde group with amide groups, followed by subsequent intercondensation to form cross-linkages and gelation. In instances where polyacrylamides are the water soluble polymer of choice, one or more of the non-aldeydic sterilants listed above are preferably included.

In general, the formulation can be comprised of 0.1 to 8.0 percent of a water-based polymer, 1 to 10 percent of the disinfectant, with the balance being deionized water. If a surfactant is used, it can be added in the range of 0.05 to 2.5 percent by weight of the total formulation preferably in the range 0.1 to 2.0 percent. If desired, an anti-oxidant such as methyl paraben or propyl paraben can be added in the range of 0.05 to 1 percent by weight of the total formulation. A dispersant such as sorbitol, glycerine, propylene glycol, and isopropanol in the range of 1 to 10 percent and preferably 3 to 8 percent by weight is used when polyethylene oxide is incorporated in the mixture.

Polyethylene oxides having molecular weights of 8,000 to 5,000,000 can be used, preferably material in the molecular weight range of 800,000 to 2,000,000 is used to achieve the desired viscosities, adhesions to organisms and lubricity. Using these molecular weights, the range of concentration can be reduced to 0.7 percent to 2 percent. Similarly, preferred molecular weights for the polyacrylamides are in the range of 200,000 to 15,000,000 at concentrations of 0.2 to 10 percent.

Surfactants that may be used in the present composition include salts of long chain alkyl sulfonic acids, salts of alkyl aromatic sulfonic acids, salts of aromatic alkyl sulfonic acids, alkyl polyoxyethyl phosphate esters, aromatic polyoxyethyl phosphate esters, mixed alkyl aromatic polyoxyethyl phosphate esters, alkylated aromatic polyoxyethylethanols, higher alkyl acetylenic glycols and their polyoxyethylethanols derivatives, salts of alkylsulfosuccinates, polyethylene oxide esters of fatty acids, salts of fatty acid amides of amino sulfonic acids, mono- and di-esters of glycerol and polyglycerols, mono- and di-esters of sorbitol, mono- and di-fatty acid esters of sorbitol, polyoxyethyl sorbitan esters, polyoxyethyl sorbitol esters, salts of alkyl polyoxyethyl ethers of propane sulfonic acid, fatty acid amides of diethanol amine, fatty acid amides of morpholine, polyethoxylated fatty alcohols, polyethoxylated fatty amines, alkyl quaternary amine halides, benzyl alkyl quaternary amine halides, and alkyl aromatic quaternary halides.

Although it is possible to have good cleansing and biocidal activity with the use of only one surfactant, it may be advantageous to use two or more different surfactants in order to thoroughly wet and coat all hard surfaces and swell any biofilm or deposited material on or within the medical device and therefore effectuate its removal. Using mixed surfactants may allow thorough wetting and swelling of the outer coat of any organism or virus, so that the sterilant can more readily penetrate and destroy that organism. For example, one may use a combination of quaternary ammonium halide with a polyethoxylated nonyl phenol, a combination of alkylbenzene sulfonate salt with an aromatic polyethoxylated phosphate ester salt. Both of these combinations may be combined with an additional long chain acetylenic glycol or polyethoxylated acetylenic glycol. Some of these combinations have the additional feature of being not only powerful detergent solutions but also contributing toward corrosion inhibition.

When glutaraldehyde is used as the biocidal agent, the biocidal activity is most rapid in alkaline solution. However, it may not be practical to operate at the higher pH levels with this reagent. Glutaraldehyde may undergo self-condensation by means of the Aldol Condensation and this rate is enhanced in an alkaline medium. Therefore, it may be preferable to keep the reaction mixtures at pH levels of 5 or lower, in order to maintain good shelf life. Preferably the pH is between about 3 to about 5 for storage. The pH may be raised to between 7 to 8 at the time of use, using sodium bicarbonate or triethanolamine as a buffer. Also, polyacrylamide may not be suitable as a polymer with glutaraldehyde for the same reasons.

Polyethylene oxide polymer chains typically are affected by oxidative degradation at the ether linkages. For this reason, an anti-oxidant may be added to solutions containing this polymer to preserve the molecular weight. Water-soluble or water-dispersible esters of parahydroxybenzoic acid, i.e., methyl or propyl paraben, are preferably used with polyethylene oxide. There are many other anti-oxidants which may be used, such as a variety of phenolic compounds, ascorbic acid, polyunsaturated compounds, and aromatic amines. Generally, combinations of aromatic amines and aldehydes should be avoided.

Another problem associated with the use of polyethylene oxides, is that they are produced as fine fluffy powders. Thus, when they are to be dissolved in water, there is a tendency for the particles to agglomerate and form intractable gels. Union Carbide, a major manufacturer of these products, has provided designs for equipment to be used in large scale operations with these polymers. However, for small scale laboratory work it is frequently more feasible to suspend the polymer powder in a non-solvent liquid, miscible with water and drip this slurry into a well-stirred water solution. For this reason, it may be practical to work with slurries of the polymer in solvents such as glycerol, propylene glycol, isopropanol, ethanol, and the like.

On the other hand, the polyacrylonitriles are produced in coarse, granular form and do not have the mechanical problems of solution experienced with the polyethylene oxides, therefore, they do not require use of the suspending solvents. Also, the polyacrylonitriles are not subject to chain degradation by oxidative cleavage and do not require anti-oxidants for preservation. In view of the above stated conditions, the following examples are provided as illustrative of, but not limiting to, the claimed composition.

EXEMPLIFICATION

Example 1

One specific formulation found to be particularly satisfactory is comprised of the following constituents in percentages by weight:

| | |
|---|---|
| 0.7% | Polyethylene Oxide, 1,000,000 MW |
| 5.0% | Denatured Ethanol |
| 4.0% | Glutaraldehyde |
| Balance | Deionized water |

When a surfactant is used in this specific formulation, it is introduced into the formulation in the following percentages by weight:

| | |
|---|---|
| 0.5% | Quaternary ammonium chloride |
| | or |
| 0.5% | Nonoxynol-9 |

Alternatively, a mixture of the two can be used at the same percentage. When an anti-oxidant is utilized, it is introduced into the formulation in the following percentages by weight:

| | |
|---|---|
| 0.2% | Methyl paraben or propyl paraben |

Example 2

Another formulation found to be particularly desirable had the following constituents in percentage by weight:

| | |
|---|---|
| 0.7% | Polyethylene oxide, 2,000,000 MW |
| 4.0% | Glutaraldehyde |
| 0.1% | Quaternary ammonium chloride |
| 0.7% | Nonoxynol-9 |
| 0.2% | Methyl paraben |
| 0.2% | Propyl paraben |
| 8.0% | Glycerine |
| Balance | Deionized water |

Example 3

Another formulation is:

| | |
|---|---|
| 0.5% | Polyacrylamide, 5,000,000 MW |
| 0.7% | Quaternary ammonium chloride |
| 0.5% | Nonoxynol-9 |
| Balance | Deionized water |

Example 4

To 21 g of polyethylene oxide having a molecular weight of about 1,000,000 add 3.75 g of methyl parahydroxybenzoate (methyl paraben) and 1.95 g of propyl parahydroxybenzoate (propyl paraben). These are ground together with a mortar and pestle and then suspended in 135 g propylene glycol and 30 g isopropanol to make a thick slurry. This slurry is then slowly poured into 2500 ml of deionized water. Stirring is continued for at least one hour to effectuate complete solution of the polymer and then 6 g polyethoxylated acetylenic glycol (such as Surfynol 440 TM, available from Air Products Co.), 3 g of an aromatic polyethoxylated phosphate ester (such as Maphos 91 TM available for Mazer Division of PPG), and 3 g of an alkylaromatic sulfonic acid (such as Biosoft-100 TM available from Stepan Chemical) are added and mixed for five minutes, then 400 g of 50% glutaraldehyde is added. The pH of this solution is about 3. Titration with 10% sodium bicarbonate may be used to bring the pH up to 7.

EXAMPLE 5

To 7 g of polyethylene oxide having a molecular weight of 2,000,000 is added 1.25 g of methyl paraben and 0.65 g of propyl paraben. These are ground together with a mortar and pestle and suspended in 45 g of propylene glycol and 15 g isopropanol to make a thick slurry. Then, 2 g of a 50% solution of dodecyl benzyl dimethyl ammonium chloride, such as BTC-50 TM, available from Stepan Chemical, is added, followed by 4 g nonoxynol-9 and 40 g 50% glutaraldehyde. This mixture is added to 925 ml of water. The pH of this solution is about 3 and it may be raised to pH 7 by titration with 10% sodium bicarbonate. In this example, propylene glycol reduces evaporation of the mixture in high speed devices, thus improving lubrication.

EXAMPLE 6

To 21 g of 2,000,000 molecular weight polyethylene oxide is added 5.8 g methyl paraben. The two are ground together with a mortar and pestle and slurried in 60 g isopropanol. The slurry is slowly poured into 2745 ml deionized water and the container is rinsed with an additional 30 ml isopropanol and poured into the stirred solution. Stirring is continued at least one hour to effect complete solution and 6.5 g of a 50% solution of dodecyl benzyl dimethyl ammonium chloride, such as BTC-50, 10 g Nonoxynol-9 ™ and 180 g 50% glutaraldehyde are added. Titration with 10% sodium bicarbonate raises the pH from 3 to 7.

EXAMPLE 7

A solution of 0.1% polyacrylamide (15,000,000 molecular weight) was prepared by slowly adding 1 g of the polymer to 850 ml well-stirred deionized water. Solution should be complete after stirring two hours. Then, 136 g of polyvinyl pyrrolidone-iodine complex (11% iodine) is slowly added to the well-stirred solution. This is followed by the addition of 1.5 grams dodecylbenzene sulfonic acid and 2 g of polyethoxylated sorbitan oleate. The solution is finally titrated with 50% triethanolamine to a pH of 6.5.

EXAMPLE 8

A solution of 0.6% polyacrylamide (5,000,000 molecular weight) is prepared by slowly adding 6 g of polymer to 850 ml deionized water. Solution should be complete after stirring 2 hours. Then, 136 g of polyvinyl pyrrolidone-iodine complex (11% iodine) is carefully stirred in, followed by the addition of 1.5 g of a linear alkane sulfonate and 2 g of an alkyl polyethoxylated sulfonic ester. Titration with 10% sodium hydroxide should bring the pH up to 6.5.

EXAMPLE 9

To 7 g of 2,000,000 molecular weight polyethyleneoxide is added 1.8 g methyl paraben and the two are ground together with a mortar and pestle. This mixture is then slurried with 45 g of propylene glycol, slowly poured in a thin stream into 900 ml deionized water. Upon complete solution, 1.5 g of dodecylbenzene sulfonic acid, 2 g of an ethoxylated nonylphenol phosphate ester, 0.6 g of an ethoxylated alkyl acetylenic glycol and 40 g of 50% glutaraldehyde are washed in with isopropanol. The resulting solution is titrated with 10% sodium bicarbonate to raise the pH from 3 to 7.

This latter Example 9, without glutaraldehyde, has the synergistic effect of providing the desired lubricity and cleaning, with a high degree of corrosion resistance for the various types of metals used in making up most modern medical devices. Although the body of most devices may be made of stainless steel, some are still made of ordinary steels and the units may also have internal components of aluminum, brass, zinc or copper. In addition, there are gaskets and seals, made of a variety of rubbers and plastics. The present composition avoids the swelling and destruction of these rubbers and plastics. The addition of glutaraldehyde creates a solution that lubricates, cleans, protects against corrosion, and disinfects and/or sterilizes.

EXAMPLE 10

Mix 1.8 g of methyl paraben and 7 g of 2,000,000 molecular weight polyethylene oxide and grind to a fine powder. Mix the powder into 45 g propylene glycol. When dispersed, mix slurry slowly into 900 ml deionized water. When solution is completely clear add 1.5 g of dodecylbenzene sulfonic acid, 2 g of ethoxylated nonylphenol phosphate ester, and 0.6 g of ethoxylated alkyl acetylenic glycol washed in with 10 ml of isopropanol. The resulting solution is buffered to pH 6.5 with triethanolamine. This formula makes a cleaner/lubricant composition. The molecular weight of the polyethylene oxide can be lowered to 8,000 without appreciable change in lubricity for medical devices that require a lower viscosity.

Formulations using polyacrylamide typically do not require dispersants or anti-oxidants. Dispersants may not be required due to the high solubility of polyacrylamide in water. Anti-oxidants may not be required since polyacrylamide is very stable; however, they may be added to enhance the corrosion resistance of the formulation.

Regarding Examples 1, 2, 4–6 and 9, the active ingredient for disinfection and/or sterlization is glutaraldehyde. The surfactants, quaternary ammonium chloride and monoxynol-9, both operate synergistically with glutaraldehyde to provide surface wetting. The two surfactants have different chemical structures and therefore provide different wetting characteristics for different kinds of proteins, and thus tend to provide a broad range of high level surface wetting which should reach most proteins. These surfactants not only make the surfaces of the proteins wet, but also swell the cells so as to receive glutaraldehyde and to make the glutaraldehyde more effective in a shorter period of time. It is believed that the surfactants provide openings in the protein in the organism, allowing the glutaraldehyde to penetrate that organism. These surfactants also act as lubricants to aid in lubrication. However, since they are surfactants, their primary purpose is to emulsify proteins, blood, other foreign matter and saliva which become attached to the internal parts of dental handpieces.

Examples 7 and 9 describe a composition that functions as a disinfectant, cleaner, and lubricant. Examples 3 and 10 describe a composition that functions as a cleaner and lubricant only. Each Example functions as a lubricant.

The disinfectant/sterilant composition can be prepared by mixing the various liquid ingredients in a vat at room temperature and stirring the same. The mixture can then be packaged in suitable containers, as for example plastic or glass bottles, and shipped in cartons for use by the dentist.

Use of the disinfectant/sterilant composition by the dentist in a method in accordance with the present invention for treating dental handpieces may now be briefly described as follows. Although the following description is directed to the use of the inventive composition in a dental device environment, the method and composition apply equally to the medical device environment and any other environment at which such a disinfecting, sterilizing, cleaning, and lubricating composition would be desirable.

In practicing the present invention, the doctor, dentist or staff member would pour a bottle of the inventive sterilizing, cleansing, disinfecting, lubricating composition into a suitable sized glass or plastic tray or other container, to such a depth that it completely cover the device lying in that container. The device would be allowed to remain immersed in the solution for at least ten hours at room temperature to achieve sterilization or at least 30 minutes if heated to 40° C. in order to achieve sterilization, and shorter periods, in the range of several minutes, if only disinfection is required. This allows the liquid to penetrate into the device. The device may be extracted from the solution and be allowed to drain on any absorbent material, such as a paper towel, for a few seconds. Any remaining free liquid may then be removed by any of a variety of means, such as wiping with a paper towel or cotton swab. In the case of a dental-handpiece it may then be reconnected to its compressed air line and excess internal liquid blown out. It would then be ready for use or if desired it could be rinsed in clean water to remove dead organisms, autoclaved then immersed in the solution after autoclaving to reestablish a chemical film on the device.

Alternatively, disinfectant/cleaner lubricating solutions may be injected into the dental-handpiece by means of any of a variety of hydraulic devices, liquid guns, or air pressure from the same source as is used to operate the device. As the liquid moves through the head of the device it disinfects, cleans and lubricates the device. At the same time it flushes any accumulated blood, saliva and other deposits, out through the opening in the head of the device. Again, after at least one minute the dental-handpiece may be disconnected from the gun and be readied for use on the next patient.

Similarly, if a compressed air gun were not available, it may be possible to inject the disinfecting lubricant into the device by means of a syringe specifically designed for the purpose, or to immerse the device in the solution in heated or unheated ultrasonic device to aid cleaning.

In another format practicing the present invention, the dentist or the dental assistant can take a container or bottle of a disinfectant or a sterilant composition of the present invention and pour the liquid mixture into a tray formed of a suitable material such as autoclavable glass or stainless steel. The tray can be of any suitable size and shape and can be rectangular in form having an open top side. It can be of a suitable size such as 4 inches in width, 8 inches in length, and approximately 3 inches in depth. The tray can be provided with a cover which can be utilized for covering the top side opening.

The dental handpiece to be disinfected in accordance with the present invention is disconnected from its compressed air line, placed in the liquid in the tray, and allowed to remain therein at room temperature for a period of at least 10 minutes, permitting the liquid to penetrate into the water and air lines and into the head of the dental handpiece. The dental handpiece may then be extracted from the liquid by suitable means such as by the use of tongs. It should be appreciated that although the human hand can be inserted into the liquid to retrieve the handpiece, this is undesirable because of the need to maintain the cleanliness or purity of the liquid in the tray.

After the dental handpiece has been retrieved from the liquid, it is permitted to drain onto a paper towel for a period of a few seconds. Any remaining liquid on the handpiece can then be removed by a suitable manner, such as paper towel or by cotton swabs. The dental handpiece is then reconnected to its compressed air lines. The air line is then turned on, blowing out the excess liquid from the air lines and the water lines and in the other parts of the dental handpiece, after which the dental handpiece can be placed in service for use with the next patient.

For lubricating purposes, the dental handpieces could be permitted to soak in the liquid disinfectant by first forcing the liquid through the dental handpiece until it appears at the head. The dental handpiece could then be permitted to soak for a period of 2 to 5 minutes, after which the gun or the syringe used to introduce the composition into the device can be utilized to force additional disinfectant into the dental handpiece to further clean, disinfect and lubricate the dental handpiece.

When a tray is used for containing liquid, it is believed that disinfectant/sterilant will be effective for at least one week and up to one month. For example, on each Monday morning, at the first of the week, the dentist or the dental assistant can take a clean tray, fill it with the inventive disinfectant/sterilant, and cover it until use. The disinfectant may be supplied so that it need not be diluted prior to use. It can be poured into the tray to the desired level and used for the entire week. At the end of the week, as for example on Friday, after the dentist has ceased work for the week, the disinfectant contained in the tray can be disposed of and the tray cleaned and dried for use on the following Monday.

The present invention is particularly efficacious for disinfecting and/or sterilizing dental handpieces to prevent the transmission of disease from one patient to the other. The disinfectant mixture also has other advantages in that it cleans out blood and saliva from inside and outside dental handpieces when used between patients. Oil-free lubrication is provided which eliminates bonding problems encountered with previous lubricants. The disinfectant mixture is also non-corrosive. Its use is advantageous because it provides extended handpiece life. It also makes possible lower operating costs for the dentist. The need for expensive oil lubricants is eliminated, which is particularly desirable because the removal of oil lubricants from dental handpieces in the past has required the use of strong solvents to clean out carbon build-up and organic matter. The water-based lubricants utilized in the disinfectant mixture of the present invention are water-soluble and can be washed out with warm water.

A sporicide test was performed on the formulation of Example 10, using the prescribed protocol of the American Organization of Analytical Chemists (AOAC). The AOAC test is used to determine sporicidal activity on EPA porcelain cylinder carriers (*Clostridium sporogenes*). The spores used were *C. sporogenes* with HCl preservative. The frozen spore suspension was diluted up to $10^5$ spores per milliliter sterile deionized water. The spore samples were aliquoted 9.0 ml into 20 mm porcelain cylinders. The cylinders were then placed into a water bath at a temperature of 45° C., for 30 minutes before initiation of the test. A control experiment was performed by aliquoting 9.0 ml sterile deionized water into a 20 ml glass test tube and was placed into 45° C. water bath.

1.0 ml of the diluted *C. sporogenes* spore suspension was added to 9.0 ml of each sample and mixed. These were then placed back into a 45° C. water bath. At each time interval, the sample was mixed and a 1.0 ml sample was taken out into 9.0 ml Fluid Thioglycollate Medium (FTM) broth containing 7.5% glycine ($10^{-1}$ dilution). A further ten-fold serial dilution was made into 9 ml broth containing 2% glycine. The data in the following Table I demonstrate the effect of exemplary contact times for the composition of Example 10 at the stated pH values.

TABLE I

AOAC SPORICIDE TEST FOR STERILIZATION
NUMBER OF CYLINDERS POSITIVES/NUMBER
TREATED WITH GERMACIDE SOLUTIONS

| Contact Time (Minutes) | pH 7 | pH 7.5 | pH 8.0 | pH 8.5 |
|---|---|---|---|---|
| 15 | 6/30 | 4/30 | 4/30 | 6/30 |
| 30 | 0/30 | 3/30 | 6/30 | 1/30 |
| 60 | 0/30 | 1/30 | 2/30 | 2/30 |

Chemosterilization is achieved for those samples having ratios of 0/30, whereas disinfection is shown for samples exhibiting ratios of 1/30 or less. Thus, chemosterilization at 45° C. is feasible at less than one hour for compositions at pH 7.0. High level disinfection at 45° C. in less than 15 minutes appears feasible.

What is claimed is:

1. A composition having lubricating and cleaning properties, comprising, in solution:
   polyethylene oxide having a molecular weight of about 2,000,000 daltons;
   methyl paraben;
   propylene glycol;
   a mixture of surfactants comprising dodecyl benzene sulfonic acid, ethoxylated nonylphenol phosphate ester, and ethoxylated alkyl acetylenic glycol;
   isopropanol; and
   water.

2. A composition having lubricating, cleaning and disinfectant properties, comprising, in solution:
   polyethylene oxide;
   glutaraldehyde;
   methyl paraben;
   propylene glycol;
   a mixture of surfactants comprising of dodecyl benzene sulfonic acid, ethoxylated nonylphenol phosphate ester, and ethoxylated alkyl acetylenic glycol;
   isopropanol; and
   water.

3. The composition of claim 2, wherein said polyethylene oxide has a molecular weight of about 2,000,000 daltons.

4. The composition of claim 2, wherein said composition is at a pH of between about 3.0 and about 7.0.

5. The composition of claim 2, wherein said polyethylene oxide constitutes, by weight, about 0.7 percent.

6. The composition of claim 2, wherein said mixture of surfactants constitutes, by weight, about 4.1 percent.

* * * * *

UNITED STATES PATENT AND TRADEMARK OFFICE
CERTIFICATE OF CORRECTION

PATENT NO. : 5,348,678
DATED : September 20, 1994
INVENTOR(S) : Hodam, Jr., et al.

It is certified that error appears in the above-indentified patent and that said Letters Patent is hereby corrected as shown below:

Col. 4, line 52, immediately following "of", insert -- a---.

Col. 6, line 45, delete "for" and insert -- from --.

Col. 8, line 23, delete "monoxynol-9" and insert -- nonoxynol-9 --.

Col. 10, line 10, immediately following "containing", insert -- the --.

Signed and Sealed this

Twenty-seventh Day of June, 1995

Attest:

BRUCE LEHMAN

Attesting Officer     Commissioner of Patents and Trademarks